(12) United States Patent
Mathis et al.

(10) Patent No.: US 8,216,211 B2
(45) Date of Patent: Jul. 10, 2012

(54) HOLDING DEVICE FOR MEDICAL INSTRUMENTS

(75) Inventors: Martin Mathis, Munich (DE); Patra Mladenovic, Karlsfeld (DE)

(73) Assignee: Brianlab AG, Feldkirchen (DE)

( * ) Notice: Subject to any disclaimer, the term of this patent is extended or adjusted under 35 U.S.C. 154(b) by 1644 days.

(21) Appl. No.: 11/539,697

(22) Filed: Oct. 9, 2006

(65) Prior Publication Data

US 2008/0086150 A1 Apr. 10, 2008

(51) Int. Cl.
*A61B 17/00* (2006.01)

(52) U.S. Cl. .......................................................... 606/1

(58) Field of Classification Search ........................ 606/1
See application file for complete search history.

(56) References Cited

U.S. PATENT DOCUMENTS

| 6,237,451 | B1 * | 5/2001 | Wei .................................. 81/490 |
| 7,166,114 | B2 * | 1/2007 | Moctezuma De La Barrera et al. .............................. 606/130 |
| 2001/0039860 | A1 * | 11/2001 | Johnson et al. .............. 81/177.4 |

* cited by examiner

*Primary Examiner* — Aaron Roane
(74) *Attorney, Agent, or Firm* — Renner, Otto, Boisselle & Sklar, LLP (57) ABSTRACT

A medical instrument holding device for holding instrument of different axial cross sections comprising a holding site unit, comprising a plurality of holding sites at predefined holding angles around an axis, the holding sites comprising different holding sizes for holding parts of instruments of different axial cross sections; and a coupling unit constituted to define a plurality of coupling angles around the axis with respect to a device support, the coupling unit being constituted to block rotational movement around the axis and to allow coupling of the holding site unit to the device support only at the plurality of coupling angles, when coupled to the device support.

12 Claims, 4 Drawing Sheets

HOLDING DEVICE FOR MEDICAL INSTRUMENTS

The present invention concerns a holding device for medical instruments, for instance biopsy needles, catheters, infusion needles, medical calibrated instruments, medical suction instruments or any other kinds of medical instruments in particular for insertion into a patient, and in particular a body structure like biological tissue (organs) or bones, in particular for injection, infusion, sample collection and surgical operations.

The instruments to be held have in particular a longitudinal section along which the shape of their cross section is constant. The shape of the cross section is in particular circular or polygonal.

For practical use it is important that the instrument is based exactly in a body structure at a target position. For this purpose, the direction of insertion is preferably exactly set. The holding device of the present invention assists in particular to set the insertion direction exactly.

An option used in surgery is the use of a stereotactic frame as a support device in order to define the orientation of the instruments with respect to the brain exactly, before the instrument is inserted along the defined orientation direction. However, under particular circumstances, a stereo tactic frame may be too bulky and too time-consuming until a defined and exact orientation is achieved. The insertion of the instruments by a surgeon in a freehand manner is generally more quick but exact placement is difficult, even if a marker unit is attached to the instrument in order to monitor the movement of the instrument. Therefore it is desired to be able to use alternative solutions in case a stereotactic frame or freehand insertion should not be preferred by a surgeon due to circumstances The holding device of the present invention, the holding system of the present invention which includes the holding device, and a navigation system of the present invention which includes the holding system allows exact orientation in an easy manner while being able to use a stereotactic frame but not being obliged to use a stereotactic frame. In particular, it is possible to insert along the same insertion channel instruments of different cross section at different times if this is needed by the surgeon. For instance, first a biopsy needle may be inserted to particular target location in the brain. In a next step, to the very same location, an infusion catheter may be inserted for treatment if the analyst of the biopsy probe reveals that the correct target has been tested.

The object of the present invention is to provide an easy usable holding device which allows holding of medical instruments of different cross section.

The aforementioned object is solved by the subject-matter of the independent claims.

Advantageously, the holding device of the present invention is used by a holding system in order to allow exact positioning of the medical instrument. Advantageously, the holding system of the present invention is used by a navigation system according to the present invention in order to navigate a medical instrument.

Advantageously, the medical instrument holding device of the present invention is for holding instruments of different axial cross sections. Preferably, a plurality of holding sites, two or more holding sites, for instance eight holding sites are provided. A plurality of holding sites, for instance a pair of holding sites may cooperate, in order to hold the same instrument. Preferably, the holding sites are arranged at predefined holding angles around an axis of the holding device. The axis is preferably a virtual (imaginary) axis but may also be a real axis of the holding device. The axis represents in particular an axis of symmetry of the structure of the holding device. The axis is in particular perpendicular to the extension direction of the longitudinal part of the instrument which is to be hold by the holding device by means of at least one of the holding sites. The aforementioned holding angles being in particular defined to be in a plane which is normal to the aforementioned axis of the holding device. In particular, the point of the plane, through which the axis passes may be considered to be the origin of a (virtual) coordinate system in which the holding angles are described. The distance between the axis and holding sites are preferably equal for each of the holding sites but may vary according to an alternative embodiment. Preferably, the angular difference of holding angles of neighboring holding sites is equal for all holding sites. Preferably, the number of holding sites divided by two is an integral number. Preferably the holding angles of the pair of holding sites which cooperate to hold an instrument differ by 180°.

Preferably, not all holding sites have the same holding sizes. The holding sites define a space through which the instrument passes and which may be narrowed in order to hold the instrument. In particular, the holding sites define a (maximum) holding space which has the (maximum) holding size. The maximum holding size defines the shape and size of the cross section of the part of the instrument which is able to be inserted. Instruments of larger cross section may not be inserted and reliably hold by the holding device. The aforementioned holding size is preferably not equal for all holding sites. Preferably, the plurality of holding sites provides for a plurality of holding sizes in order to be able to hold instruments of different axial cross section, in particular different size of the axial cross section. As mentioned above, a number of holding sites, in particular two holding sites may cooperate to hold an instrument of the same axial cross section. This means, that this cooperating holding sites have preferably the same holding size.

As will be explained in more detail in the detailed description, the holding sites are preferably constituted to vary the holding size. In particular, they are constituted to narrow the (maximum) holding size in order to hold instruments having a cross section smaller than the maximum holding size. The preferred variation of the holding size, in particular below the maximum holding size is kept within a predefined range in order to achieve sufficient accuracy as will be discussed later in the detailed description of embodiments.

The medical instrument holding device of the present invention preferably comprises a coupling unit. The coupling unit is preferably constituted such that a plurality of coupling angles are provided which define an allowed angular relationship between the holding device and a device support to which the holding device may be coupled. Preferably, the coupling unit is constituted to block a rotation around the aforementioned axis of the holding device. The coupling unit can achieve the rotation blocking for instance mechanically by form fitting (form closure or positive locking), by means of a snap mechanism, by magnetic force interaction etc. The coupling unit preferably cooperates with a support device in order to define the plurality of coupling angles. This means that coupling between the device support and the holding device is only possible at the defined coupling angles. In order to achieve this, the coupling unit comprises preferably a plurality of rotation blocking members which are arranged around the axis, the angular difference between the location of the blocking members correspond preferably to the angular difference of the coupling angles. Preferably, the coupling angles are defined in a plane normal to the axis of the holding device as discussed above with respect to the holding angles.

Preferably, the angular difference between holding angles of neighboring holding sites is equal to the angular difference between neighboring coupling angles or between the position of rotation blocking members. Preferably, the number of holding sites corresponds to the number of coupling angles. Preferably each of the rotation blocking members cooperate with coupling angle members of the device support by e.g. mechanical interaction or magnetic interaction. For instance a rotation blocking member is a projection which is insertable in a coupling angle member constituted as a recess. Another example is that the rotation blocking member is a magnet which is attracted by a coupling angle member which also is a magnet. Another particularly preferred example for rotation blocking members are the edges or surface sections of a polygon structure which represents the coupling angle members.

The above-mentioned coupling unit may be constituted to block only a rotational movement, when coupled to the support device, while allowing relative translational movements between the holding device and the support device. This represents a preferred embodiment. The relative translational movement is in particular along the axis of the holding device. In particular, in case this translational movement is allowed due to the structure of the coupling unit, according to a preferred embodiment, a fastening unit is provided which allows to block a relative translational movement between the holding device and the support device, in particular along the axis, when the holding device is coupled to the support device.

Preferably, the holding device of the present invention further comprises a fastening unit which is constituted to fast and/or fix the holding device to the support device. The fastening is preferably performed mechanically, in particular by fastening mechanisms using threads (for instance screws) and a releasable snap mechanisms. Alternative fastening units represent magnets or press fitting mechanisms.

Preferably, the holding sites are constituted by an inner and outer holding unit, the inner holding unit being closer to the support device than the outer holding unit, when the holding device is coupled to the support device in use for holding an instrument. The inner holding unit and the outer holding unit cooperate to define inner and outer parts of the respective holding sites. Preferably, the inner holding unit comprises a number of inner parts of the holding sites which coincide with the number of holding sites and the outer holding unit comprises a number of outer parts of the holding sites which coincides with the number of holding sites. The respective inner parts of the holding sites are associated to corresponding outer parts of the holding sites. Respectively, one inner part and one outer part cooperate to define a particular (maximum) holding size of the plurality of different holding sizes provided by the holding device of the present invention.

Preferably, the fastening unit is constituted to press the outer holding unit towards the inner holding unit, when the holding device is fastened to the support device. For this purpose, the outer holding unit is arranged between the inner holding unit and the fastening unit, when the holding device is coupled to the support device and in particular fastened to the support device. Preferably, the fastening unit is arranged more away from the support device than the inner holding unit.

According to the preferred embodiment, the fastening unit comprises a fastening member which is rotatable relative to the holding sites of the holding device, in particular rotatable relative to the outer holding unit, when the fastening member is coupled or contacting the outer holding unit. This applies in particular when the fastening member is agitated in order to achieve fastening of the holding device or to release a fastened holding device from the support device. Preferably, the fastening member is coupled to the reminder of the holding device, in particular to the outer holding unit in a manner which results in a translational coupling. This means, there is a coupled movement of the holding sites and the fastening member by movements along the axis of holding device while a rotational movement of the fastening member relative to the holding sites is possible.

Preferably a marker unit which is usable by a navigational system and which comprises at least two, preferably at least three markers (e.g. balls) which may actively emit or preferably passively reflect radiation (e.g. light, in particular infrared light) or waves (in particular sound waves or ultra sound waves) are attached or part of the elements of the holding device. The marker units allow the detection and in particular also the identification (due to the particular special relationship between the markers) of the elements. A marker unit may be attached to at least one of the following means or may be integer with the at least one of the following means: holding site unit, inner holding unit, outer holding unit, fastening unit, support device, support arm structure, one or more elements of a support device, in particular of the support arm structure, joints of the support arm structure as mentioned, each holding site may be constituted by means of the inner and outer holding unit. The inner and outer holding unit represent in particular separable parts. More than two parts, i.e. an additional part in addition to the inner and outer holding may be used in order to constitute a holding site. The holding site unit is in particular constituted to hold the instrument by means of form fitting and/or press fitting. Preferably, in case the maximum holding size of the holding site corresponds to the cross section of the instrument, press fitting and form fitting is combined. In case the cross section is smaller, advantageously, the instrument is hold by press fitting. According to one example, there are provided at least three contact points or contact lines along which there is a contact in order to achieve a press fitting of the instrument and in order to define an exact location of the instrument relative to the holding device, in case the cross section of the instrument is smaller than the maximum holding size.

Preferably each of the holding sites comprises a recess member and a projection member. The recess member may have a polygonal structure but has preferably at least an arcuate section. In particular, the recess member comprises a section in the form of a U. The projection member comprises preferably in its projecting end facing the recess member also a recess which may be arcuateor polygonal and has preferably a V shape. Preferably the inner holding unit has only one of the recess member and projection member while the outer holding unit has the other one of the recess member and projection member. For instance, the inner holding unit only has recess members while the outer holding unit only has projection members.

Preferably the projection member and its associated counterpart, the recess member are constituted such that the projection member is insertable in the corresponding recess member. According to a preferred embodiment of the invention, not all projection members are insertable in all recess members due to the different sizes provided for the holding sites. This assures that the inner holding unit and outer holding unit are used in a correct manner by the operator. For this purpose, for instance, at least one of the projection members has an extension in circumferential direction of the holding size unit (i.e. around the axis) which is larger than the extension of at least one of the recess members, at least of that part of the recess member which defines the holding size (e.g. the U part of the recess member). Preferably, the extension in circumferential direction of the projection member is such that only one relative position in circumferential direction is possible in order to couple the inner holding unit with the outer holding unit for defining the holding sites. In particular, the extension of the second smallest projection (at least that part which defines the holding site) is larger in circumferential direction than the extension of the smallest recess (in particular larger than that part of the recess which defines the holding site).

Preferably, as mentioned above, at least two holding sites cooperate to hold the same instrument. Preferably, the holding space of each of the at least two holding sites is arranged along a straight line along which an instrument to be held will be located. The straight line is preferably such that it crosses the axis of the holding device. Preferably, the two cooperating holding sites are arranged on opposite sites of the axis, preferably in equal distance to the axis.

Preferably, the present invention relates to a holding system which comprises the aforementioned holding device and the device support for supporting the holding device. Preferably, the device support comprises a support coupling unit constituted for coupling with the coupling unit of the holding device (also called: "holding device coupling unit"). In particular, the support coupling unit is constituted to assist the coupling of the holding device coupling units, in particular the coupling mechanism (rotation blocking member) of the holding device coupling unit. For instance, the support coupling unit comprises a polygonal structure which allows for form fitting with a corresponding polygonal structure of the holding device coupling unit. In particular, the support coupling unit comprises members like edges and/or surface sections of a polygon to define the coupling angles in cooperation with the coupling unit of the holding device. Alternatively, as mentioned above, the support coupling unit may comprise for instance recesses while the holding device coupling unit comprises projections (or vice versa) which cooperate to define the plurality of coupling angles. Furthermore, the support coupling unit may for instance comprise magnets which cooperate with magnets of the holding device coupling unit. Preferably, the device support comprises a first support member and a second support member. The first support member is preferably rotatable relative to the second support member. The first support member preferably comprises the support coupling unit. The second support member is preferably for linking with the support device, e.g. the support arm structure. The axis of rotation preferably coincides with the axis of the holding device. This allows for exact placement of the holding system in three dimensional space. Preferably, the device support has the rotation around the axis as the only degree of freedom in order to ease the aforementioned placement process.

The present invention preferably also relates to a navigation system. The navigation system preferably comprises the aforementioned holding system. Furthermore, the navigation system preferably comprises a detection unit in order to detect at least one marker unit of the holding system. Furthermore, the navigation system preferably comprises a data processing unit connected with the detection unit. The data processing unit is constituted to process the data of the detection unit in order to determine the location of the holding system, in particular the location of at least one of the holding sites, in particular the location of the holding site into which an instrument is inserted or is to be inserted. Preferably, the holding system and/or holding device and/or holding site unit comprise at least one marker unit which is detected by the detection unit. Preferably, the location of the holding site which is the uppermost with respect to the axis of the holding device is detected. Preferably, additionally or alternatively, the location of the instrument is detected by means of markers integrated in the instrument and/or (e.g. releasable) attached to the instrument. Preferably also marker units attached to the support arm structure and are detected in order to determine the exact position of the holding system, in particular at least one of the holding sites. Preferably, the navigation system is used in order to assist exact positioning of the holding system, in particular of the instrument by giving information on the deviation between a current position and a target position of the holding system. Preferably, proposals for changes and/or information on deviations with respect to each of the joints or at least some of the joints used are given by means of a user interface (e.g. screen, sound system, etc.). Of course, preferably, the navigation system of the present invention comprises a user interface for user data input (e.g. keyboard) and output of data (e.g. screen).

In the following detailed description of the invention, further features of the invention are disclosed. Different features of different embodiments may be combined.

Figure 1:
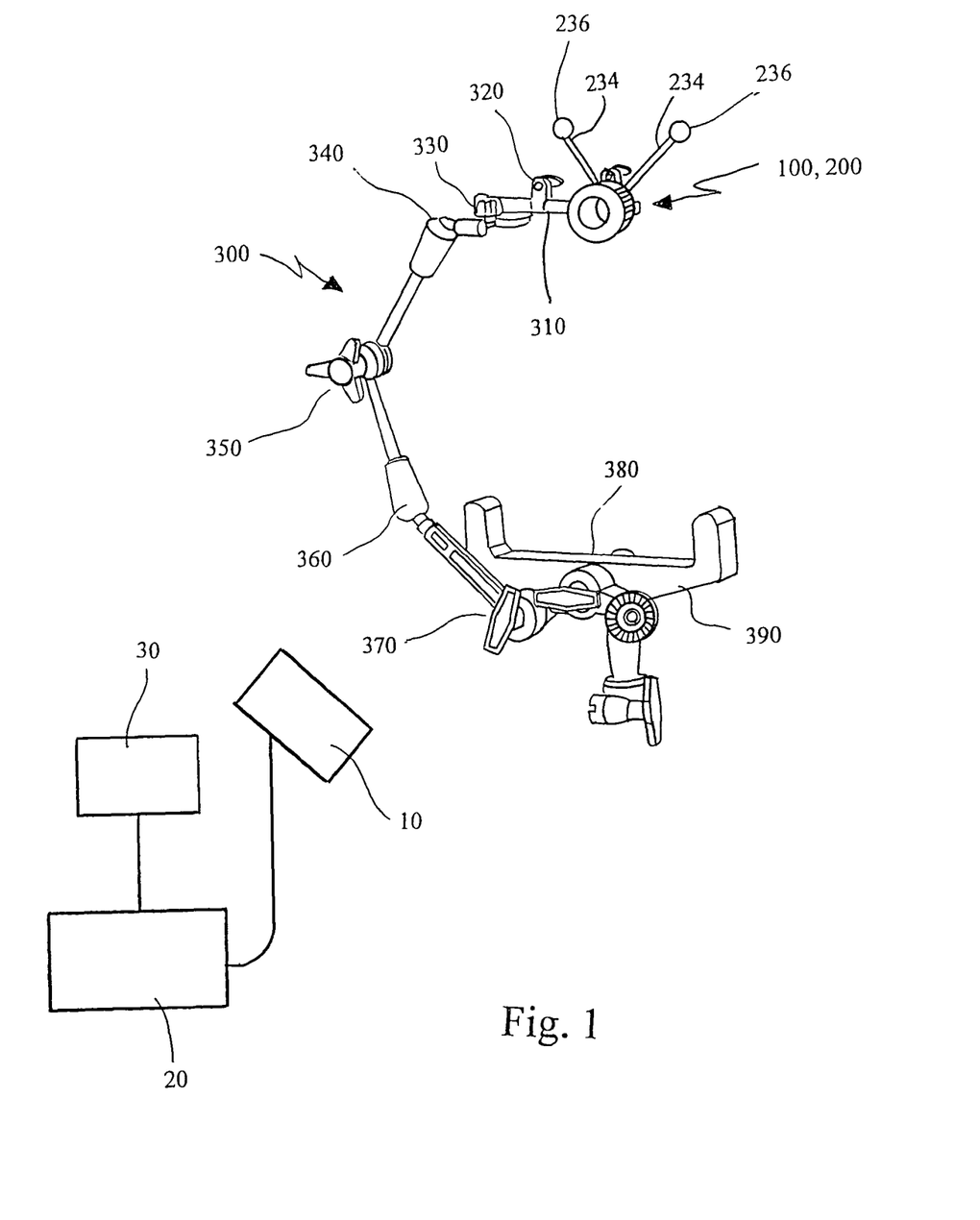
FIG. 1 shows an embodiment of a navigation system of the present invention, a support arm structure, a holding system of the present invention and a holding device of the present invention.

FIG. 1 shows a setup for positioning biopsy needles. An embodiment of the holding system 100, 200 of the present invention is attached to the end 310 of a flexible support arm structure 300. Joints 320, 330, 340, 350, 360, 370, and 380 allow a free positioning of the end 310 of the support arm structure. For instance, the head of a patient may be placed between the embodiment of the invention 100, 200 and a support bracket 390 of the support arm structure 300 which supports the arm of the support arm structure 300. The holding system 100, 200 of the present invention is constituted to a hold biopsy needle in order to position at the needle exactly in the head of the patient. Alternatively to the support arm structure other support devices like stereotactic frames may be used in order to hold the holding device or holding system of the present invention.

Besides the support arm structure other parts of a navigation system of the present invention is shown. A detection unit, in particular camera unit 10 is connected to a data processing unit 20 which processes the detection data. The camera 10 detects for instance infrared light reflected from marker units, in particular from marker balls 236 shown in FIG. 1 or other marker balls 1, 2, 3, 4, 5 and 6 shown in FIG. 5. The data are processed in known manner in order achieve a navigation of the holding system in three-dimensional space. In particular and optionally and not obligatory, the navigation system may be used to register the inner disc 110 by using a pointer as described when discussing FIG. 4 below. Information for the user based on the processed data is shown on a screen 30.

Figure 2:
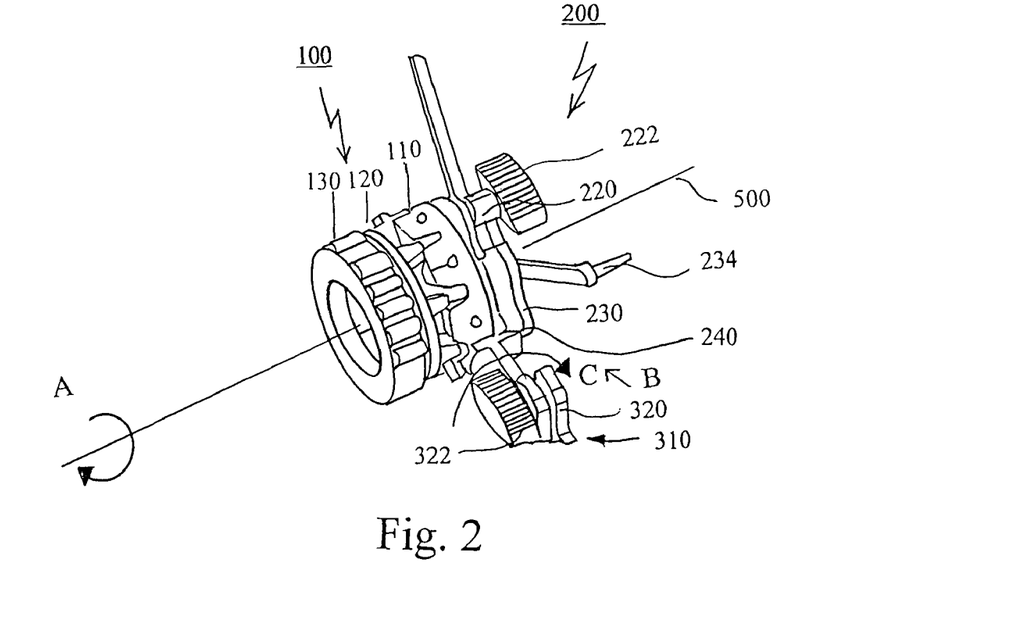
FIG. 2 shows a holding system of the present invention.

The holding system of the present invention is shown in more detail in FIG. 2. The holding system of the present invention comprises a holding device 100 (shown in dark grey) and a device support 200 (shown in light grey). The device support 200 is attached to the end 310 of the support arm structure 300 (shown in FIG. 1) by the joint 320. Loosening of the joint 320 allows movement of the device support 200 in the directions B (translational) movement and D (rotational movement).

The device support 200 comprises a joint 220 which may be loosened by the screw 222 in order to achieve a rotational movement A around an imaginary axis 500. Preferably, a joint is provided which allows only rotation around the axis 500 and to do not allow movements concerning other mechanical degrees of freedom. Since, in case the holding device is fastened to the support device, the axis 500 corresponds to the axis of symmetry of the holding system, an exact positioning is made easier. In the embodiment shown in FIG. 2, the device support 200 comprises two parts, a part 230 and a part 240. The part 230 is rotatable relative to the part 240 around the axis 500. The part 230 is connected with a leg 234 of a reference array which allows the attachment of marker balls (of a marker unit) at its end. The marker balls are detectable by a navigation system and are in particular passive reflecting marker balls which reflect for instance light.

The holding device 100 shown in FIG. 2 consists of three parts which are called inner disc 110, outer disc 120 and lock ring 130. The combination of the inner disc 110 and the outer disc 120 represent an example for a holding site unit. The inner disc 110 and outer disc 120 are used for defining holding sites for holding the instruments (e.g. biopsy needle). The lock ring 130 is used for both fastening the holding device 100 to the device support 200 and for clamping an instrument at the selected holding site.

Figure 3:
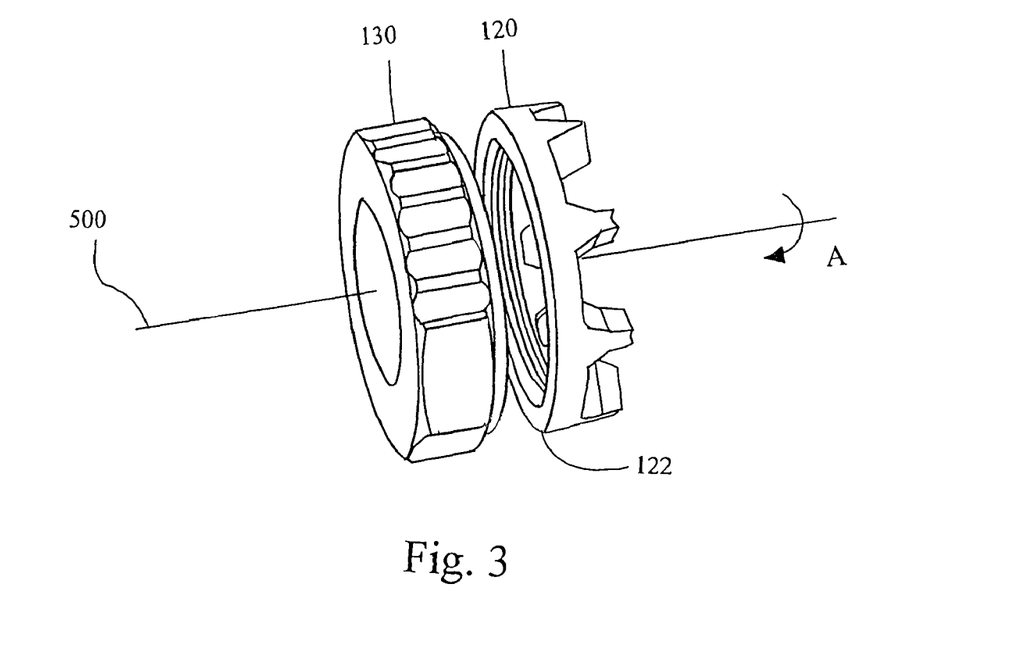
FIG. 3 shows a lock ring and outer disc.

FIG. 3 shows the lock ring 130 and the outer disc 120 in more detail. In particular it is obvious from FIG. 3 that the lock ring 130 and outer disc 120 are detachable from each other. Preferably, the lock ring 130 and the outer disc 120 may be coupled by means of a snap mechanism. A snap projection (not shown) is provided in the lock ring 130 which may snapingly engage into a groove 122 of the outer disc 120. If coupled by the snap mechanism, a relative translational movement along the axis 500 of the outer disc 120 and the lock ring 130, which would separate the lock ring 130 from the outer disc 120, is blocked. On the other hand, the projection (not shown) may slide in the groove 122 in order to allow a rotational movement of the lock ring 130 relative to the outer disc 120 around the axis 500 in the rotational direction A (or counterwise to A).

Figure 4:
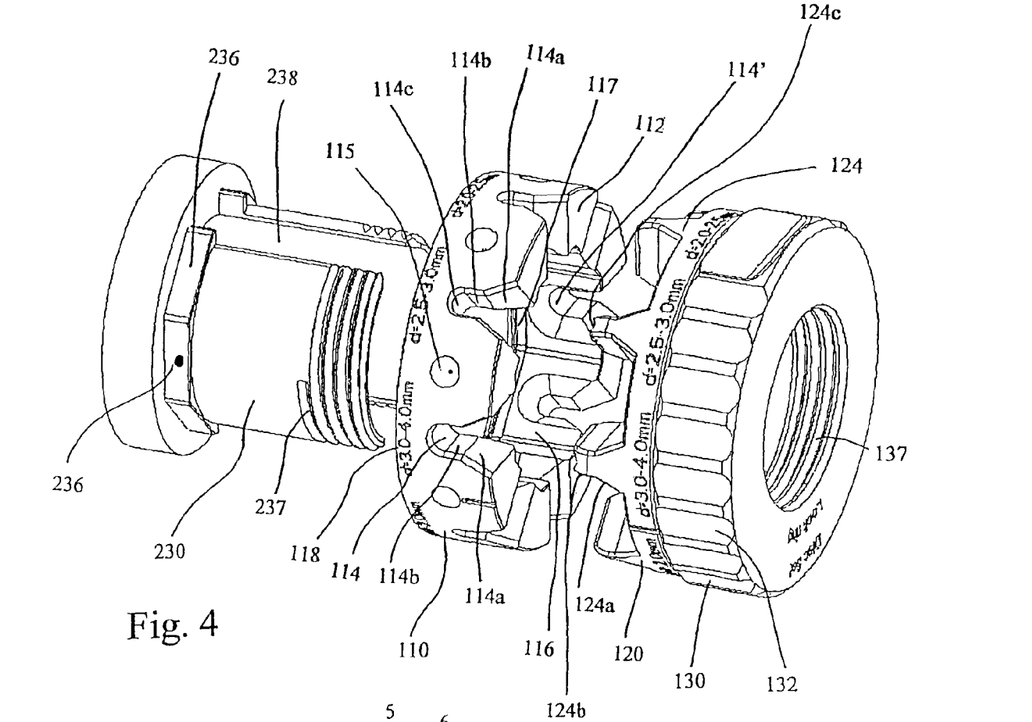
FIG. 4 shows a holding system of the present invention before fastening of the holding device to the device support.

FIG. 4 shows an embodiment of the holding system of the present invention. The part 230 of the device support 200 is separated from the inner disc 110. The inner disc 110 is separated from the outer disc 120 which is coupled to the lock ring 130.

The inner disc 110 is formed in a ring-like manner. In the example shown, the outer circumference of the inner disc 110 follows the path of a circle or ring. The wall of the inner disc 110, the outer circumference of which follows the path of the circle or the ring will be referred to as ring wall in the following. The ring wall has two end faces. An inner end face which faces the device support 200 and an outer end face 112 which faces the outer disc 120. Furthermore the ring wall has the outer circumference (called "outside of the ring wall") and the inner circumference (called "inside of the ring wall"). The inner end face of the ring wall is preferably continuously and shaped as a ring. The outer end face 112 is interrupted by recesses 114. The recesses 114 cooperate with corresponding, insertable projections in order to form holding sites for the instruments and to define the holding spaces in particular of a particular (maximum) holding size. The recess 114 represents an example for an inner part of a holding site. Preferably, the recesses 114 consist of three parts. An outer part 114*a* of the recess 114 which has the shape of a cone-like recess and comprises two walls (called "truncated walls" 114*a*) facing each other and being inclined towards the inner side (i.e. towards the device support 200) such that they become more and more closer towards the inner side. A second part 114*b* (called "parallel walls" 11*b*) of the recess 114 is preferably formed by two parallel walls which are aligned parallel to an axis. The axis coincides with the aforementioned axis 500 in case the holding device is fastened to the support device. The axis of the inner disc 110 is preferably the central axis of the ring wall. Preferably, all recesses 114 are equidistant to the axis of the inner disc 110. The third part 114*c* (called "ring section wall" 114*c*) of the recess 114 is preferably shaped like a ring section and connects the parallel walls 114*b*.

The inner disc 110 comprises a plurality of recesses. In the example shown there are eight recesses. Preferably, the recesses are located at opposing sides (with respect to the axis of the inner disc) and are identical in shape. Preferably, the recesses, in particular the ring section walls 114*c* of opposing recesses are aligned along a straight line which passes through the axis of the inner disc such that a rod shaped instrument having circular cross section the diameter of which coincides with the diameter of the ring wall section 114*c*, abuts against the two ring section walls 114*c* which are located opposite to each other. In the example shown in FIG. 4, the recesses designated as 114 and 114' are located opposed to each other and are identical in shape and size.

Since in the example given in FIG. 4, all recesses and projections located at opposing sides of the axis are identical in shape and size, there are provided four different sizes of holding spaces (i.e. half of total number of recesses) along the ring wall of the inner disc.

This allows to insert instruments of different cross sections into the respective recess pairs (114 and 114') which are located opposed to each other.

As can be seen by the inscription at reference number 118, the recess 114 (and its opposing counterpart 114') are meant for accommodating the rod shape part of an instrument which has a cross section between 3.0 mm and 4.0 mm. This means in case of a diameter of 4.0 mm the rod shape instruments fully contacts the ring section wall 114*c*, i.e. the radius of the ring section wall 114*c* coincides with the radius of the rod shaped instrument.

Preferably, the recesses 114, and in particular the ring section walls 114*c*, the parallel walls 114*b* and the truncated walls 114*a* extend in a groove-like manner towards the axis of the inner disc in order to define a channel for inserting and holding a rod-shaped instrument. This extension in a groove-like manner is preferably longer than the diameter defined by the ring section walls in order to have a good guidance and stability of the held instrument.

Furthermore, pointer recesses 115 are provided which allow the insertion of a pointer in order to register and/or calibrate the holding device. This feature is optional. Generally, the position of the holding device is known due to a fixed spatial relationship between the holding device and the device support. In that case, the pointer recesses may be used (optionally) to check the correctness of the known position. Pointers are for instance instruments having a marker unit of two or more markers (e.g. marker balls). The spatial relationship between the markers and the tip of the pointer is known. The pointer is observed by a navigation system, in particular comprising a camera, when the tip of the pointer is inserted in the pointer recesses 115. In this way, the location of the inner disc 110 may be registered in three dimensional space and/or the type of holding device, in particular the type of inner disc may be identified. Different type of holding devices, in particular inner discs (and corresponding outer discs) may vary in the size of the recesses in order to allow differently sized instruments to be held. In case the holding device is fastened to the device support 200, the location of the recesses 114 may be determined from the location of the pointer recesses 115. The registration process thus enables the location of an instrument held by the holding device of the present invention to be determined. For instance, the pointer recesses may have particular and e.g. unique spatial relationship with respect to each other allowing to determine which of the printer recesses is close to which of the holding sites (114, 124).

The ring wall of the inner disc 114 is ring-shaped at the outside while it is polygonal-shaped at the inside. The inside has n plane sections 116 arranged in a closed loop. In more detail, in the example (n=8) shown in FIG. 4, the inside of the ring wall has an octagonal shape (n=8). The octagonal shape is defined by eight adjoining plane sections 116 extending parallel to the axis of the inner disc and surrounding the axis in equal distances from the axis. The arrangement of plane sections, i.e. the planes represent an example for the holding device coupling unit. Each plane section 116 comprises one of the recesses 114. Preferably the recesses 114 extend in the middle of the plane sections 116 of the polygonal (in particular octagonal) inside of the inner disc towards the holding device 100 and parallel to the axis of the inner disc. The axis of the inner disc 110 (and also of the lock ring 130 and of the outer disc 120) coincide with the axis 500 of FIG. 1, in case the holding device 100 is fastened to the device support 200.

The polygonal inside of the inner disc 110 comprising in particular plurality of plane sections 116 (and representing an example for a coupling unit) is preferably constituted to mutely engage with a polygonal structure 236 of the part 230 in order to achieve at least partly a form closure (form fitting) between the holding device 100 and the device support 200. The engagement may be for instance such that the polygonal inside of the inner disc 110 encompasses and in particular contacts the polygonal structure 236 when the holding device is fastened to the device support. In this way, when fastened, a relative rotation between the part 230 and the inner disc 110 is blocked due to a polygonal form fitting (form closure) between the polygonal structure 236 and the polygonal inside of the inner disc 110. Thus, a rotation around the axis 500 may be blocked and in particular a definite angular relationship between the holding device 100 and the device support 200 may be set (i.e. one of the plurality of coupling angles may be selected). Preferably, the polygonal structure 236 and the polygonal inside of the inner disc 110 are complementary shaped. Preferably, the polygonal structure is such that the angles defined by the edges of the polygon are equal. This allows to set a distinct number of relative angles between the device support and the inner disc (or holding device). Preferably the difference between adjoining relative angles is equal (e.g. 45° in case of octagonal structure).

In the example shown, an octagonal structure allows to set eight different relative angles (coupling angles) between the device support 300 and the holding device 100.

In order to achieve a coupling in the axial direction between the inner disc 110 and the part 230 of the device support 200, a coupling mechanism may be provided. The coupling allows to releasably block movement in the axial direction and to set a fixed spatial relationship in the axial direction. As shown in FIG. 4, a ball 236 representing a press bearing which presses the ball outwards, i.e. away from the axis 500, is provided in one of the (eight) plane faces of the polygonal structure 236. The ball 236 may be pressed inwards in order to attach the inner disc 110 to the part 230 of the device support 200. The ball 236 engages with a groove 117 provided in the polygonal inside of the inner disc 110, i.e. in the plane sections 116 of the polygonal inside of the inner disc. The groove 117 is preferably arranged close to the end face of the inner disc 110 which faces the part 230 of the device support 200, i.e. is preferably close to the inner end face.

The outer disc 120 shown in FIG. 4 (and FIG. 3) has projections 124 meant for the insertion into the recesses 114 of the inner disc 110 in order to form holding sites for the instrument. The projections 124 represents an example for an outer part of the holding site. The projections 124 are shaped preferably but not obligatory such that the outer end faces 112 of the inner disc 110 may come in contact with the inner end faces (not shown) of the outer disc 120 which face towards the inner disc. Projections 124 consist of three parts, a first part 124a which is formed complementary or approximately complementary to the truncated wall 114a of the inner disc. The truncated walls 124a of the outer disc at opposite side of each projection are inclined towards each other in the inner direction, i.e. towards the device support. Subsequent to the truncated walls 124a there are parallel walls 124b which further extend towards the inner side, i.e. towards the device support. The end of the projection 124 which faces the inner disc 110 and in particular the ring sections wall 114c has a V fornation 124c. The open side of the V is meant to face a compatible ring section wall 114c.

The distance between the open ends of the V formation 124c corresponds approximately to the diameter of the associated ring section wall. Preferably and not obligatory, the distance between the open ends of the V formation 124c is between 80% or 90% and 100% of the diameter of the associated ring section wall 114c, preferably between 95% and 100%, more preferably between 98% and 100%. Preferably the ring section walls 114c extend along half of a circle such that the ends of the ring section wall define a full diameter of a circle which corresponds to a maximum diameter of an instrument insertable in the holding space. In particular a maximum holding size for a rod shaped instrument is defined by the maximum diameter.

The V formation in corporation with the ring section wall 114c allows to set rod shaped instruments of varying diameters into the holding site which is respectively formed by a ring wall section 114c of a inner disc 110 and a V formation 124c of the outer disc 120. Furthermore the surface of the ring wall section 114c and the surface of the V formation 124c define the holding space for holding the instrument and the available holding size. In case the diameter of the cross section of the rod shaped instrument is less than the diameter of the ring section wall 114c, a contact at least three points between the instrument and the inner and outer disc 110, 120 is assured due to the geometry of the ring section wall 114c and the V formation 124c. As shown in FIG. 4 at reference sign 118, the corresponding recess 114 is suitable to accommodate rod shaped instruments, the cross section of which correspond exactly to the ring section wall (in the example 4.0 mm) as well as rod shaped instruments of smaller diameter below 4.0 mm. The preferred minimum diameter is in the example 3.0 mm. Preferably, the minimum diameter is about 10% to 30% or 40% smaller than the maximum diameter, more preferably at maximum 25% smaller than the maximum diameter in order to assure exact positioning of the instrument. Due to providing a plurality of holding sites which are easily changeable for an operator, the range between the preferred minimum diameter and the maximum diameter may be reduced.

Figure 5:
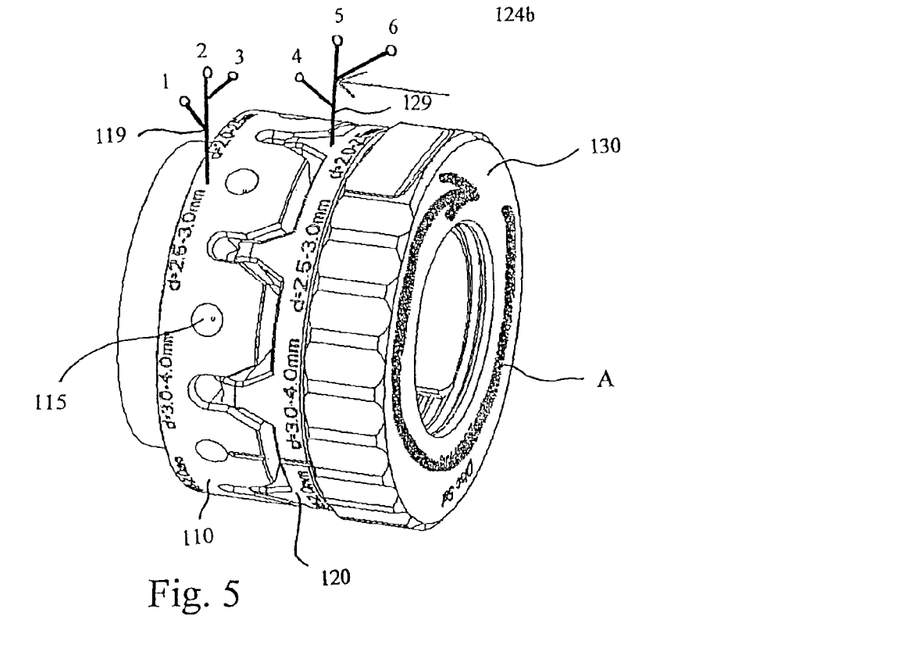
FIG. 5 shows the fastening of a holding device to the device support.
Figure 6:
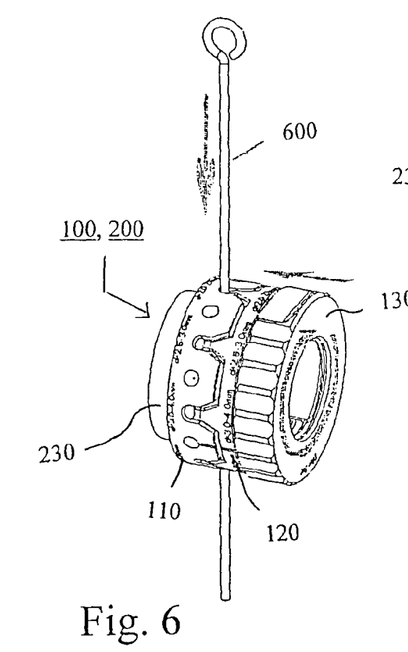
FIG. 6 shows an instrument held by the holding system of the present invention.

In case an instrument is inserted between the inner and outer disc as can be seen in FIG. 6, the distance between the inner disc 110 and the outer disc 120 may vary in dependence on the diameter of the held instrument. In case the diameter of the instrument is equal to the maximum diameter of the recess in which the instrument is held (i.e. clamped between 114c and 124c), then there is a maximum use distance between the inner disc 110 and the outer disc 120 when the holding device is fastened to the device support in use. This maximum distance is reduced if the instrument is replaced by an instrument of smaller diameter which is held within the same recess. This results in a shift of the center (imaginary) axis of the rod shaped instrument with respect to the part 230 of the device support 200. In order to measure and detect this shift, a reference array 119 comprising at least one marker, preferably a marker unit of plurality of markers may be attached or integrated in the outer disc 120. This is shown as a marker unit 129 in FIG. 5 which is attached to the outer disc 120. Furthermore, an option is to attach a marker unit 119 to the inner disc 110. Alternatively or additionally the pointer recesses 115 may be checked by a pointer or may be replaced by markers, in particular of different size. By using the marker units 119 and 129, the relative position of the inner disc 110 and outer disc 120 may be detected. In particular based on the detection of the marker unit 119 and/or 110 it may be automatically detected which of the holding sites is used for holding an instrument in order to determine the position of the instrument and/or cross section of the instrument, in particular by (additionally) detecting a marker unit attached to the instrument. In particular, a shift of the central axis of the instrument may be detected by using the marker unit 129. The position of the marker unit 129 relative to the marker unit 119 of the inner disc and/or the marker unit 234 of the device support may be used in order to determine the positional shift of the central axis of the instrument. Furthermore, depending on the shift of the central axis with respect to the position of the central axis in case an instrument of maximum diameter is inserted in one of the recesses, it may be determined whether the inserted instrument is within the preferred range, i.e. whether the diameter of the instrument is above or equal to the preferred minimum diameter. In case, the instrument is below the preferred minimum diameter, this may be detected and a user information procedure may be initiated by the navigation system. In particular, a proposal may be given to choose another holding site more suitable for the instrument, i.e. where the diameter is within the preferred (and proposed) range of diameters. In particular, a warning signal may be issued.

Alternatively to or additionally to providing the marker units 119 and/or 129 at the inner disc and/or outer disc, for instance an RFID detection unit may be provided which contacts a RFID chip in the instrument in order to determine its type, in particular the cross section of its rod part to be hold or held. Based on the data and based on the detection of the used recess, it may be determined whether the inserted instrument or instrument to be inserted is within the preferred holding size range or not and whether the navigation system should for instance initiate the above-mentioned procedure to warn and/or inform the user if the instrument is outside the preferred range. Preferably, the navigation system assumes that a holding site at a predefined holding angle with respect to the device support, e.g. the uppermost holding site, is the site intended for holding the instrument and/or the navigation system determines by means of a marker unit comprised by the instrument which holding site is used by the instrument.

As described with respect to FIG. 3, the lock ring 130 may be rotated relative to the outer disc 120. The lock ring 130 comprises hand-gripping faces 132 which ease the rotation of the lock ring for an operator. This hand-gripping faces are provided on the circumferential outside of the lock ring 130. The circumferential inside of the lock ring 130 is provided with a thread 137. The grooves of the thread 137 surround in a spiral manner the axis 500 which represents in particular an axis of symmetry in case the holding device is fastened to the device support. The thread 137 is constituted to engage with a complementary thread 237 provided on the part 230 of the device support 200. The complementary thread 237, as shown in FIG. 4 is provided on the outside of two walls which represent sections of a cylinder which surrounds the aforementioned axis 500. The sections are separated by a gap 238 in order to allow the passing of an instrument. Thus the distance of the gap is preferably equal or larger than the extension of the largest holding size in circumferential direction. Preferably, the extension of the thread in axial direction is longer than the extension of the lock ring 130. This allows the held instrument to be loosened while still having a reliable seat of the lock ring 130 on the thread 237. Loosening of the instrument allows the position of the instrument to be adjusted, in particular perpendicular to the axis of the holding device.

When the lock ring 130 is rotated as shown by the arrow A in FIG. 5, and if the thread 137 is in contact with the complementary thread 237 of the part 230 while the inner disc and outer disc are between the part 230 and the lock ring 130 (as shown in FIG. 4), then the inner disc, outer disc and lock ring are fastened to the part 230 while the projections 124 engage in their complementary recesses 114 as shown in FIG. 5.

As shown in FIGS. 4 and 5, due to the octagonal structure and the equal shape of opposing recesses or projections, four different diameter ranges for attaching an instrument are provided by the holding device according to the invention.

Preferably, an instrument 600 as shown in FIG. 6 has a particular orientation relative to the part 230 of the device support 200. The present invention allows this relative orientation to be maintained while using instruments 600 of different cross section. This is done by rotating the inner disc 110 with respect to the part 230 in one of the plurality of attachable positions (in the example 8 possible positions). In the shown example, the inner disc is rotated such that the uppermost (and thus also the lowermost) recess has a diameter range suitable for the instrument to be attached. The outer disc 120 is brought into an angular relationship with respect to the inner disc 110 such that all (complementary) projections 124 fit into their complementary recesses when the outer disc 120 is moved towards the inner disc when the lock ring 130 is rotated to engagement with the thread 237. The sense of rotation is shown as A.

Figure 7:
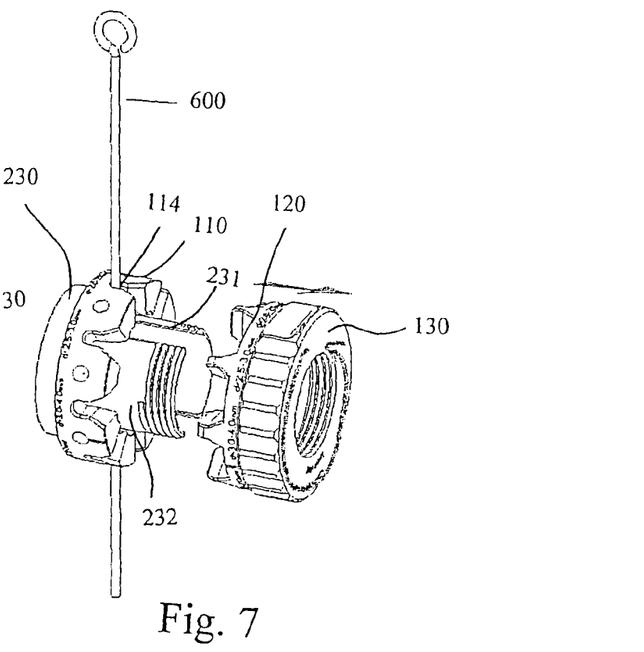
FIG. 7 shows releasing of the lock ring and the outer ring from the instrument.
Figure 8:
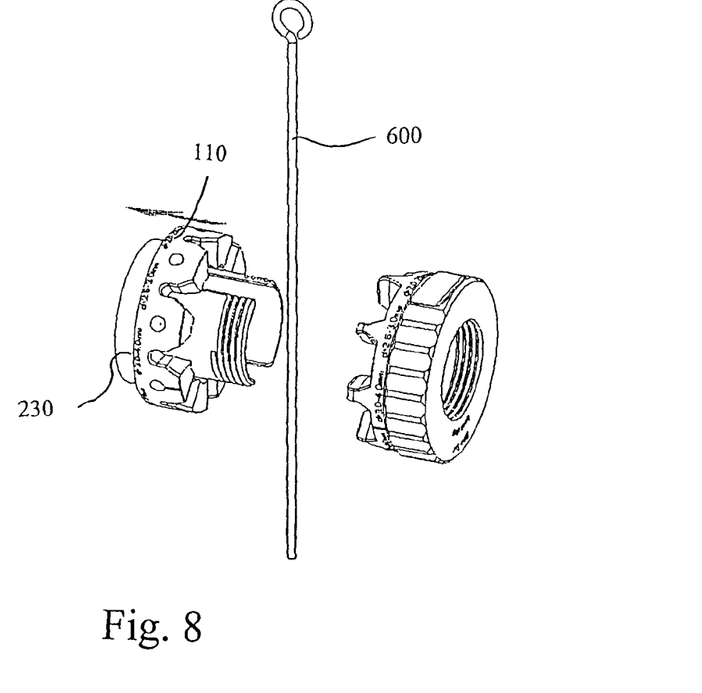
FIG. 8 shows releasing of the inner ring and device support from the instrument.

FIG. 7 shows detachment of the instrument 600 from the inner disc 110. The instrument 600 passes through a recess 114 and through the gap 238 in the two cylindrical sections 231 and 232. In the situation shown in FIGS. 6 to 8 it may be assumed that the instrument 600 has not only be attached to the holding system of the present invention 100, 200 but that the end of the instrument is inserted in a biological tissue, e.g. brain of a patient. In this situation, it may be preferred to remove the holding system of the present invention. For this purpose, the ring lock is rotated in direction A' (which is counter to the sense of rotation for fastening) in order to detach the ring lock 130 from the part 230 of the device support 200 as shown in FIG. 7. Since the ring lock 130 is coupled with the outer disc 120 by a snap mechanism, the ring lock 130 automatically removes (catches) the outer disc 120 when the ring lock is detached. The inner disc 110, together with the part 230 of the device support 200, may then be detached from the instrument 600 as shown in FIG. 8. The instrument 600 stays in the biological tissue for further use.

The invention claimed is:

1. A medical instrument holding device for holding instruments of different axial cross sections, said instrument holding device couplable to a device support and including a holding site unit, the holding site unit comprising:
   a) a plurality of holding sites each arranged at predefined holding angles around an axis;
   b) a coupling unit defining a plurality of coupling angles around the axis with respect to the device support, wherein when coupled to the device support said coupling unit is configured to
      i) block rotational movement of the coupling unit around the axis and
      ii) allow coupling of the holding site unit to the device support only at one of the plurality of coupling angles; and
   c) an inner holding unit and an outer holding unit operable to move with respect to each other and directly contact and directly and fixedly hold therebetween parts of instruments having axial cross sections of different sizes.

2. The holding device according to claim 1, further comprising a fastening unit for fastening the holding device to the device support.

3. The holding device according to claim 2,
   wherein when the coupling unit is attached to the device support the inner holding unit is closer to the device support than the outer holding unit, and
   wherein when in use for holding an instrument the inner holding unit and outer holding unit define respectively an inner part and an outer part of the respective holding sites.

4. The holding device according to claim 3, wherein when fastening the holding device to the device support the fastening unit is configured to press the outer holding unit towards the inner holding unit.

5. The holding device according to claim 2, further comprising a translational coupling member configured to couple the fastening unit to the holding site unit in the axial direction.

6. The holding device according to claim 1, wherein the holding sites are arranged along a circle around an axis of the holding device, the axis passing in a direction normal to and through the center of the circle.

7. The holding device according to claim 2, further comprising a trackable marker unit attached to or integral with at least one of the holding site unit, an inner holding unit of the holding site unit, an outer holding unit of the holding site unit, the fastening unit, or the device support.

8. A holding system comprising the holding device of one of the preceding claims and the device support, the device support comprising a support coupling unit for coupling with the coupling unit of the holding device.

9. A navigation system comprising the holding system of claim 8;
   a detection unit for detecting marker units;
   a data processing unit for processing detection signals of the detection unit in order to determine a position of at least parts of the holding device and/or for navigating the holding device.

10. The navigation system according to claim 9, further comprising a user interface for outputting information, wherein the data processing unit is configured to calculate deviations between a target position of the holding device and a current position of the holding device, and wherein the user interface is configured to output information corresponding to the calculated deviations.

11. A medical instrument holding device for holding instruments of different axial cross sections, said instrument holding device couplable to a device support and including a holding site unit, the holding site unit comprising:
   a) a plurality of holding sites each arranged at predefined holding angles around an axis;
   b) a coupling unit defining a plurality of coupling angles around the axis with respect to the device support, the coupling unit including a positioning member engageable with a corresponding positioning member of the device support at any one of a plurality of angularly rotated positions corresponding to the coupling angles and when engaged precluding rotational movement of the coupling unit relative to the device support; and
   c) an inner holding unit and an outer holding unit operable to move with respect to each other and directly contact and directly and fixedly hold therebetween parts of instruments having axial cross sections of different sizes.

12. The holding device according to claim 11,
   wherein when the coupling unit is attached to the device support the inner holding unit is closer to the device support than the outer holding unit, and
   wherein when in use for holding an instrument the inner holding unit and outer holding unit define respectively an inner part and an outer part of the respective holding sites.

\* \* \* \* \*